(12) United States Patent
Levine et al.

(10) Patent No.: US 6,661,967 B2
(45) Date of Patent: Dec. 9, 2003

(54) VARIABLE TEMPERATURE VAPORIZER

(75) Inventors: Lawrence T. Levine, Easton, CT (US); Kristopher J. Stathakis, Scottsdale, AZ (US); Christopher J. Wolpert, Scottsdale, AZ (US); Carl Triplett, Scottsdale, AZ (US); Mengtao Pete He, Scottsdale, AZ (US); Debra Park, Mesa, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 09/792,507

(22) Filed: Feb. 23, 2001

(65) Prior Publication Data

US 2001/0053283 A1 Dec. 20, 2001

Related U.S. Application Data

(60) Provisional application No. 60/184,817, filed on Feb. 25, 2000.

(51) Int. Cl.[7] .............................. F24F 6/08; H05B 3/02
(52) U.S. Cl. ...................................... 392/395; 219/482
(58) Field of Search .............................. 392/386, 387, 392/390, 394, 395; 219/482, 483, 484, 485, 490, 504, 505, 509, 510

(56) References Cited

U.S. PATENT DOCUMENTS

| | | | |
|---|---|---|---|
| 1,994,821 A | | 1/1935 | Blaise |
| 1,994,932 A | | 3/1935 | Vidal |
| D159,407 S | | 7/1950 | Costello |
| 2,597,195 A | | 5/1952 | Smith |
| 2,611,068 A | | 9/1952 | Wellens |
| D189,420 S | | 12/1960 | Diehl |
| 3,375,774 A | * | 4/1968 | Fujimura et al. ............ 219/505 |
| 3,400,252 A | * | 9/1968 | Hayakawa et al. .......... 219/504 |
| 3,476,293 A | * | 11/1969 | Marcoux ..................... 219/504 |
| 3,527,924 A | * | 9/1970 | Lutz ............................ 219/504 |
| 3,564,205 A | * | 2/1971 | Tyler ........................... 219/499 |
| 3,584,196 A | * | 6/1971 | Kurokawa et al. .......... 219/435 |
| 3,651,308 A | * | 3/1972 | Kurokawa et al. .......... 219/505 |
| 3,872,280 A | | 3/1975 | Van Dalen |
| 3,943,331 A | * | 3/1976 | Meijer ......................... 219/499 |
| 4,316,080 A | * | 2/1982 | Wroblewski ................ 219/505 |
| 4,467,177 A | | 8/1984 | Zobele |
| 4,663,315 A | | 5/1987 | Hasegawa et al. |
| 4,724,976 A | | 2/1988 | Lee |
| 4,731,520 A | | 3/1988 | Glucksman et al. |
| 4,739,928 A | | 4/1988 | O'Neil |

(List continued on next page.)

FOREIGN PATENT DOCUMENTS

| | | |
|---|---|---|
| WO | WO 91/15249 | 3/1991 |
| WO | WO 98/19526 | 11/1997 |
| ZA | 968433 | 10/1996 |

*Primary Examiner*—Sang Paik
(74) *Attorney, Agent, or Firm*—Snell & Wilmer LLP

(57) ABSTRACT

The present invention suitably provides a method and apparatus for controlling the temperature of a liquid vaporizer heating element, and thereby the rate of evaporation and level of fragrance delivery from the same. In accordance with one exemplary embodiment of the present invention, the device may include a switch that suitably allows the temperature of various types of heating elements to be controlled for different levels of fragrance output. For example, an exemplary embodiment may include a two-pronged plug adaptable to typical outlets that might be found in residential homes or businesses. In accordance with another exemplary embodiment of the present invention, the electrical switch generally provides varying resistance values to the electric circuitry of the vaporizer such that, by changing the switch setting, the operating temperature of the wick is controlled and thus the rate of fragrance evaporation from the vaporizer.

6 Claims, 11 Drawing Sheets

U.S. PATENT DOCUMENTS

| | | | |
|---|---|---|---|
| 4,745,705 A | | 5/1988 | Yamamoto et al. |
| 4,874,924 A | * | 10/1989 | Yamamoto et al. ......... 392/395 |
| D307,180 S | | 4/1990 | Luthy |
| 5,016,772 A | | 5/1991 | Wilk |
| 5,038,394 A | | 8/1991 | Hasegawa et al. |
| 5,050,762 A | | 9/1991 | Giorgi |
| 5,095,647 A | | 3/1992 | Zobele et al. |
| 5,111,477 A | | 5/1992 | Muderlak |
| 5,161,646 A | | 11/1992 | Aurich et al. |
| D335,530 S | | 5/1993 | Schimanski |
| 5,222,186 A | | 6/1993 | Schimanski et al. |
| 5,290,546 A | | 3/1994 | Hasegawa et al. |
| D346,207 S | | 4/1994 | Martin |
| D357,330 S | | 4/1995 | Wong et al. |
| 5,484,086 A | | 1/1996 | Pu |
| 5,591,395 A | | 1/1997 | Schroeder et al. |
| D381,443 S | | 7/1997 | Yuen |
| 5,647,053 A | | 7/1997 | Schroeder et al. |
| D386,974 S | | 12/1997 | Wefler |
| D393,063 S | | 3/1998 | Wefler |
| 5,773,795 A | | 6/1998 | Messmer |
| D407,476 S | | 3/1999 | Goeren et al. |
| 5,909,845 A | | 6/1999 | Greatbatch et al. |
| 5,926,614 A | | 7/1999 | Steinel |
| 5,940,577 A | | 8/1999 | Steinel |
| 6,104,867 A | | 8/2000 | Stathakis et al. |

* cited by examiner

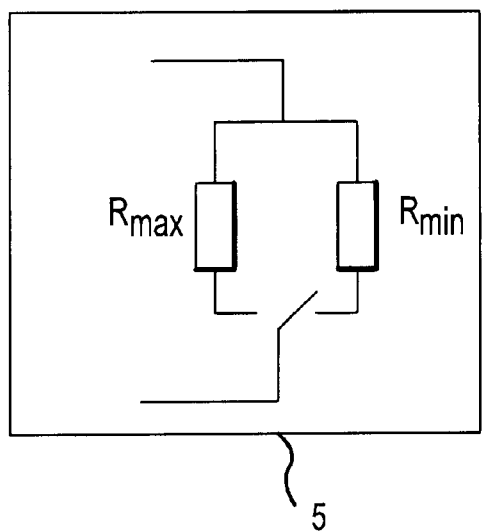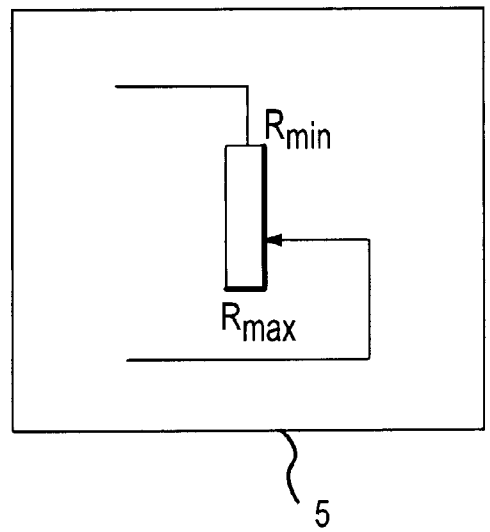
FIG.12A  FIG.12B
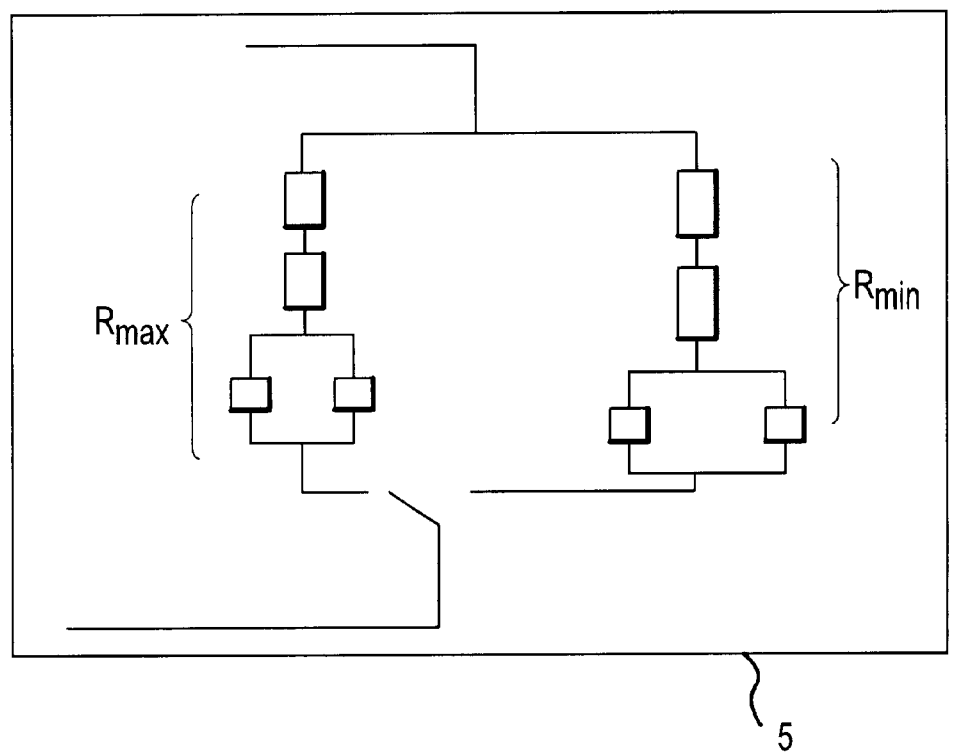
FIG.12C

VARIABLE TEMPERATURE VAPORIZER

CROSS REFERENCES TO RELATED APPLICATIONS

This application claims priority to U.S. Provisional Patent Application Serial No. 60/184,817 entitled "Electrical Plug-In Vaporizer" filed Feb. 25, 2000.

BACKGROUND OF THE INVENTION

1. Field of the Invention

The present invention relates generally to liquid vaporizers for dispensing volatile liquid materials such as fragrance oils and solutions, deodorants, insecticides and the like, and, more particularly, the present invention relates to a method and apparatus for controlling the rate of liquid evaporation.

2. Background of the Invention

Electrical liquid vaporizers (often referred to as "liquid electrics") are generally well known in the prior art. Typically, such electric liquid vaporizers comprise a housing unit configured to receive a bottle or liquid container portion. The bottle portion contains a wick or wicking system through which the volatile liquids can be migrated to a portion of the wick that is exposed to the air. The exposed portion of the wick is generally heated by a heating element disposed within the housing unit and proximate to the wick in order to suitably facilitate the vaporization of the volatile liquid to be dispensed therefrom.

Various methods for attempting to control the rate of evaporation of volatile liquids have been designed and marketed for electric liquid vaporizers. For example, some electric vaporizers have an annular collimation mechanism to mechanically control the orifice size, while others have means to mechanically control the position of the wick relative to the heating element. However, such mechanical controlling devices have generally been found to be somewhat ineffective in controlling the rate of liquid evaporation. Alternatively, other electric liquid vaporizers use an electrical switch to turn the electrical power on and off; however, the electrical ON/OFF switch does not provide different evaporation rates for variable delivery of fragrance intensity. Polarized plugs are desirable for liquid vaporizers employing a wick that must be oriented vertically or substantially upright. Furthermore, for safety concerns, polarized plugs are desirable if an electrical ON/OFF switch is part of the unit in that inadvertent polarity reversal might permit the device to operate while in the "OFF" setting. The need for a polarized plug also tends to complicate the assembly process. In some applications, the polarized plug may not be an optimum choice for plug-in air fresheners because of a lack of convenience to users. For example, there are often outlets that are not compatible with the vaporizer having a polarized plug or where the polarity of the outlet has been unknowingly reversed (e.g., those in older residential homes or those with polarity misoriented).

In attempting to control the rate of evaporation of volatile liquids from an electric liquid vaporizer, it is also be desirable to have means for compensating for voltage and/or current fluctuations in order to substantially maintain (once set) a temperature suitably adapted for a user-selected level of fragrance delivery.

Thus, the prior art, taken either alone or in combination with existing delivery systems, fails to teach approaches that permit effective control of the rate of evaporation and the level of fragrance intensity.

SUMMARY OF THE INVENTION

The present invention suitably provides a method and apparatus for controlling the temperature of a liquid vaporizer heating element, and thereby the rate of evaporation and level of fragrance delivery from the same. In accordance with one exemplary embodiment of the present invention, the device may include a switch that suitably allows the temperature of various types of heating elements to be controlled for different levels of fragrance output. For example, an exemplary embodiment may include a two-pronged plug adaptable to typical outlets that might be found in residential homes or businesses. In accordance with another exemplary embodiment of the present invention, the electrical switch generally provides varying resistance values to the electric circuitry of the vaporizer such that, by changing the switch setting, the operating temperature of the wick is controlled and thus the rate of fragrance evaporation from the vaporizer.

BRIEF DESCRIPTION OF THE FIGURES

Additional aspects of the present invention will become evident upon reviewing the non-limiting embodiments described in the specification and the claims taken in conjunction with the accompanying figures, wherein like numerals designate like elements, and:

FIGS. 12A, 12B and 12C are alternative embodiments of fragrance switches in accordance with the present invention;

DETAILED DESCRIPTION OF EXEMPLARY EMBODIMENTS

The following descriptions are of exemplary embodiments of the invention only, and are not intended to limit the scope, applicability, or configuration of the invention in any way. Rather, the following description is intended to provide convenient illustrations for implementing different embodiments of the invention. As will become apparent, various changes may be made in the function and arrangement of the elements described in these embodiments without departing from the spirit and scope of the invention. For example, various changes may be made in the design and arrangement of the elements described in the preferred embodiments without departing from the scope of the invention as set forth in the appended claims.

In general, the present invention provides a method for controlling the temperature and/or the rate of evaporation of a volatile liquid in a vaporizer device. For example, as described further herein and in accordance with various exemplary embodiments of the present invention, a method for dispersing a volatile substance is provided in which a vaporizing device generally comprises a heating element for heating the substance to be dispersed and means for varying the temperature of the heating element in order to control the rate of delivery of volatile substance from the vaporizer.

Figure 1:
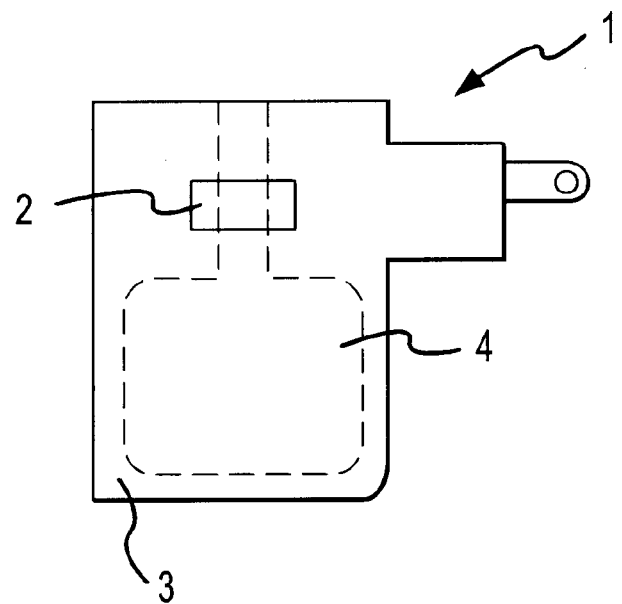
FIG. 1 is a side view of a unitary vaporizer device in accordance with the present invention.
Figure 2:
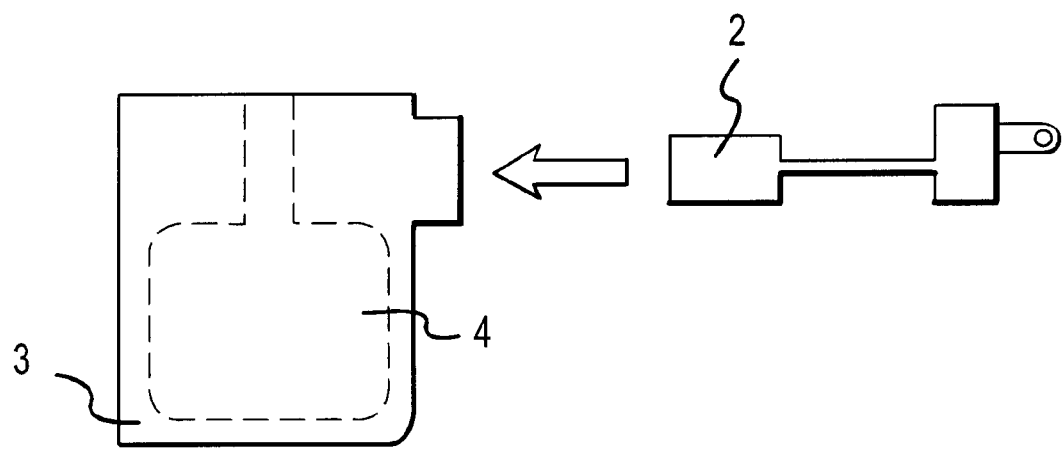
FIG. 2 is a side view of another exemplary embodiment of a vaporizer device in accordance with the present invention.
Figure 3:
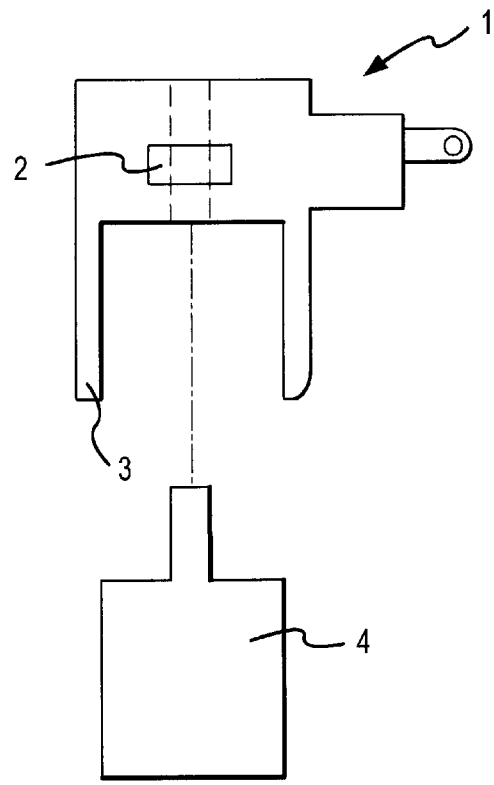
FIG. 3 is a side view of another exemplary embodiment of a vaporizer device in accordance with the present invention.
Figure 4:
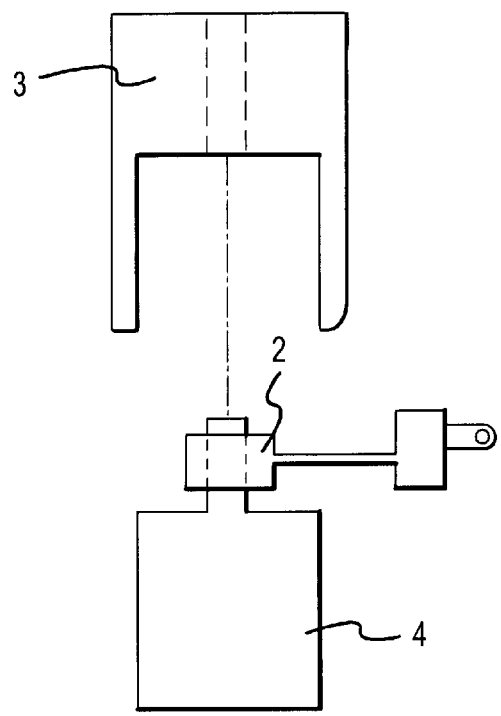
FIG. 4 is a side view of another exemplary embodiment of a vaporizer device in accordance with the present invention.
Figure 5:
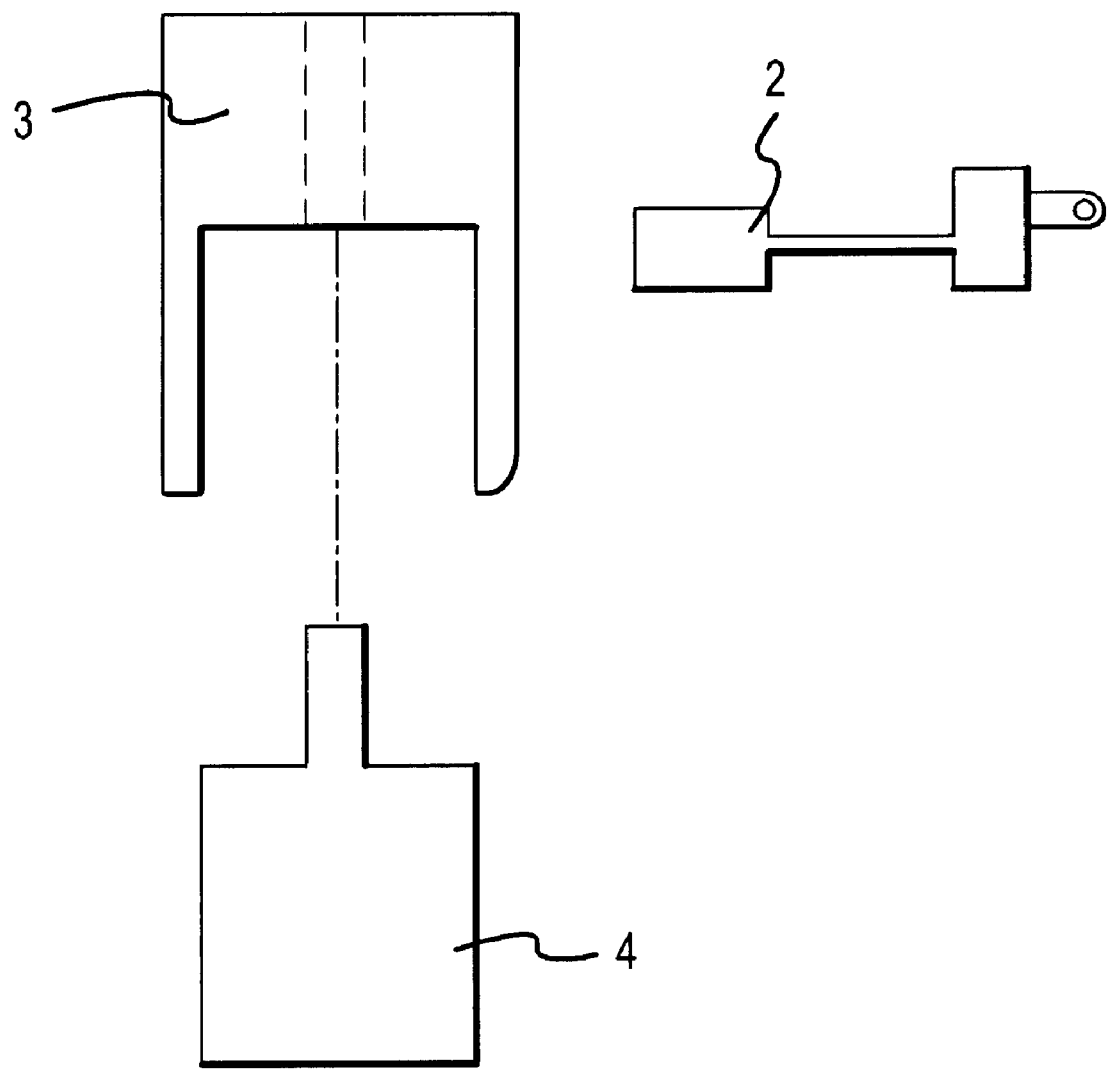
FIG. 5 is a side view of another exemplary embodiment of a vaporizer device in accordance with the present invention.

For example, in one exemplary embodiment, a vaporizing device 1 may be comprised of a heating element 2, a support structure 3 and a volatile substance reservoir 4 in a substantially unitary configuration as depicted in FIG. 1. In an alternative embodiment, as shown in FIG. 2, vaporizer device 1 may be comprised of support structure 3 and reservoir 4 in a unitary configuration suitably adapted to engage with heating element 2. In yet another alternative embodiment, vaporizer 1 may be comprised of support structure 3 and heating element 2 in a unitary configuration suitably adapted to engage with reservoir 4 as shown in FIG. 3. In still another alternative exemplary embodiment, vaporizer 1 may be comprised of support heating element 2 and reservoir 4 in a unitary configuration suitably adapted to engage with support structure 3 as depicted in FIG. 4. In another exemplary embodiment of the present invention, vaporizer 1 may be comprised of heating element 2, support structure 3 and reservoir 4 each suitably adapted to independently engage with the other as generally depicted in FIG. 5. Thus, these and many alternative configurations which fall within the scope of the present invention are possible.

Heating element 2 may generally be comprised of a resistor, a plurality of resistors in series or in parallel, an induction coil or any other means for electrically generating heat now known or hereafter devised by those skilled in the art. Additionally, support structure 3 may further comprise structural and/or functional features to facilitate delivery of the volatile substance from the vaporizer 1 such as a channel, semi-permeable membrane or any other means for directing or expelling a vapor now known or hereafter devised by those skilled in the art. In the exemplary embodiments described herein, such features are generally described as a wick.

In one exemplary embodiment, the reservoir 4 may comprise a solid, liquid, gas or gel carrier in which a volatile substance may be suspended. Reservoir 4 may further comprise an integral wick, capillary tube, at least partially exposed surface area or any other structural feature now know or hereafter devised by those skilled in the art for directing the migration of volatile substance from the reservoir 4 to an area generally proximate to heating element 2. Exemplary volatile substances may include fragrances, disinfectants, sanitizing agents, insect repellants, insecticides, pharmaceutical preparations or any other substance having a vapor pressure suitably adapted for delivery from a vaporizer device 1 now known or hereafter devised by those skilled in the art.

Figure 7:
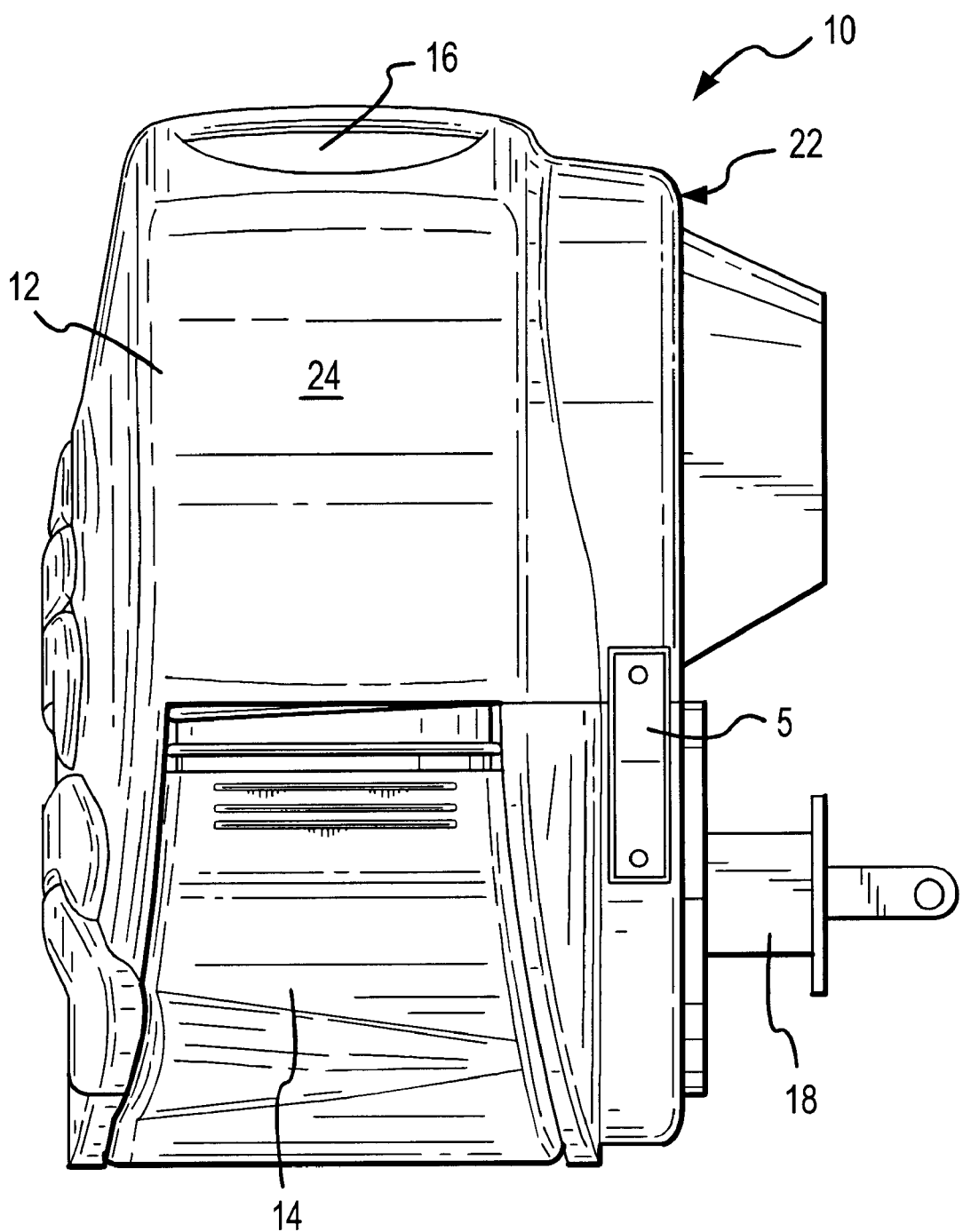
FIG. 7 is a side view of an electric liquid vaporizer with a resistor-type heating element in accordance with another exemplary embodiment of the present invention.

In other contemplated exemplary embodiments, the present invention comprises an electric liquid vaporizer 10 that includes an electrical switch 5 that, as described in further detail herein, suitably allows the rate of evaporation of the liquid in the vaporizer to be varied. For example, an exemplary embodiment of switch 5 is shown in FIG. 7. Switch 5 generally accomplishes this by changing the amount of energy applied to a heating element of the vaporizer 10, thereby changing the evaporation rate. The temperature range is important because above the foregoing range, vaporizer 10 tends to release more fragrance than desired, which may reduce the length of life for the product. However, in contrast, when the temperature falls below the specified range, vaporizer 10 may not meet the demand of those who desire a more densely fragranced environment.

With reference back to FIG. 6, liquid vaporizer system 10 suitably comprises a housing unit 12 and a refill bottle unit 14. As shown, refill bottle unit 14 is suitably configured for disposition within housing 12 and for retention therein.

Figure 8:
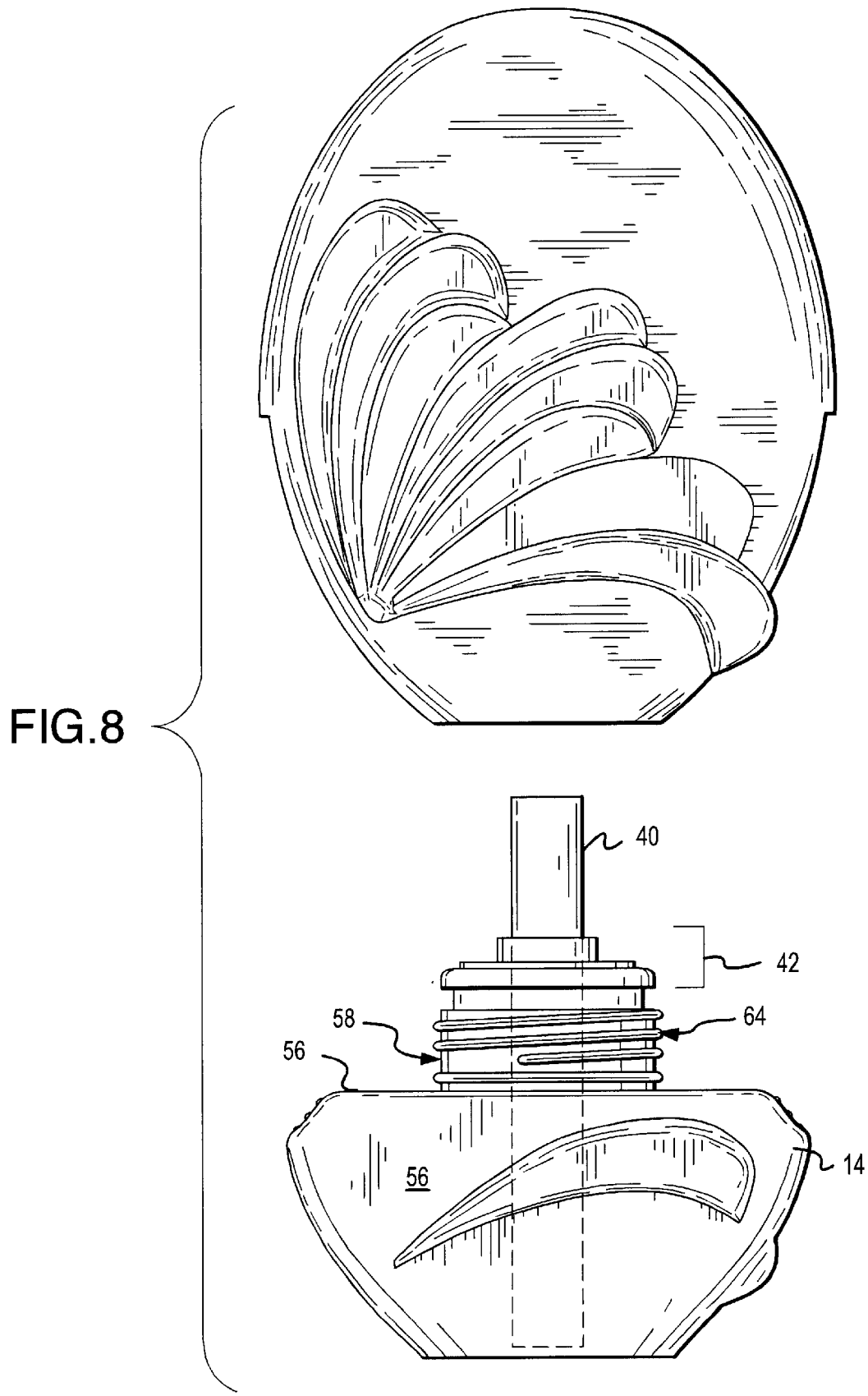
FIG. 8 is an exploded front view of the liquid vaporizer of FIG. 6, showing a bottle and a housing, which comprise a liquid vaporizer in accordance with the present invention.
Figure 10:
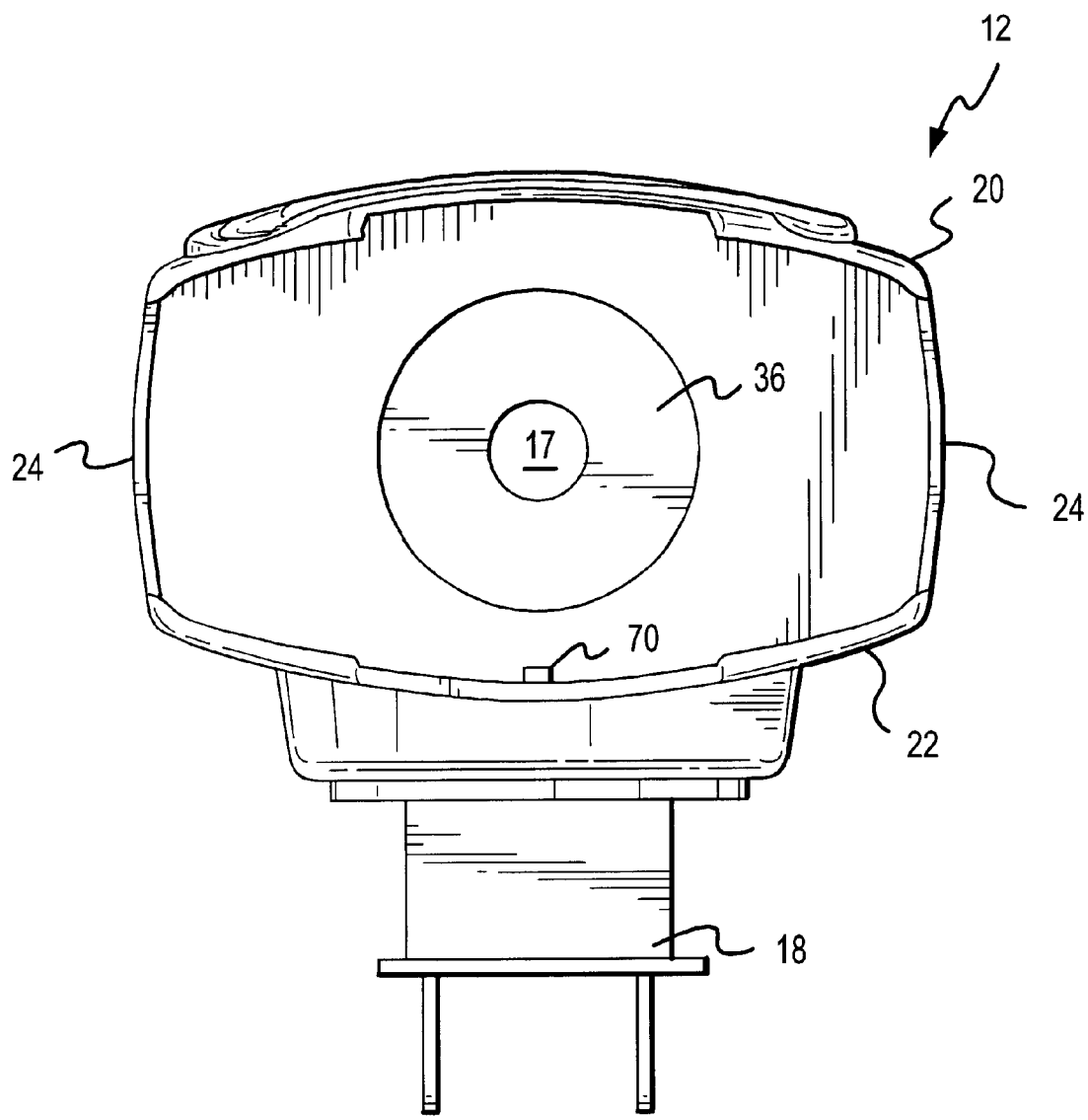
FIG. 10 is a bottom view of the housing unit of FIG. 9.
Figure 11:
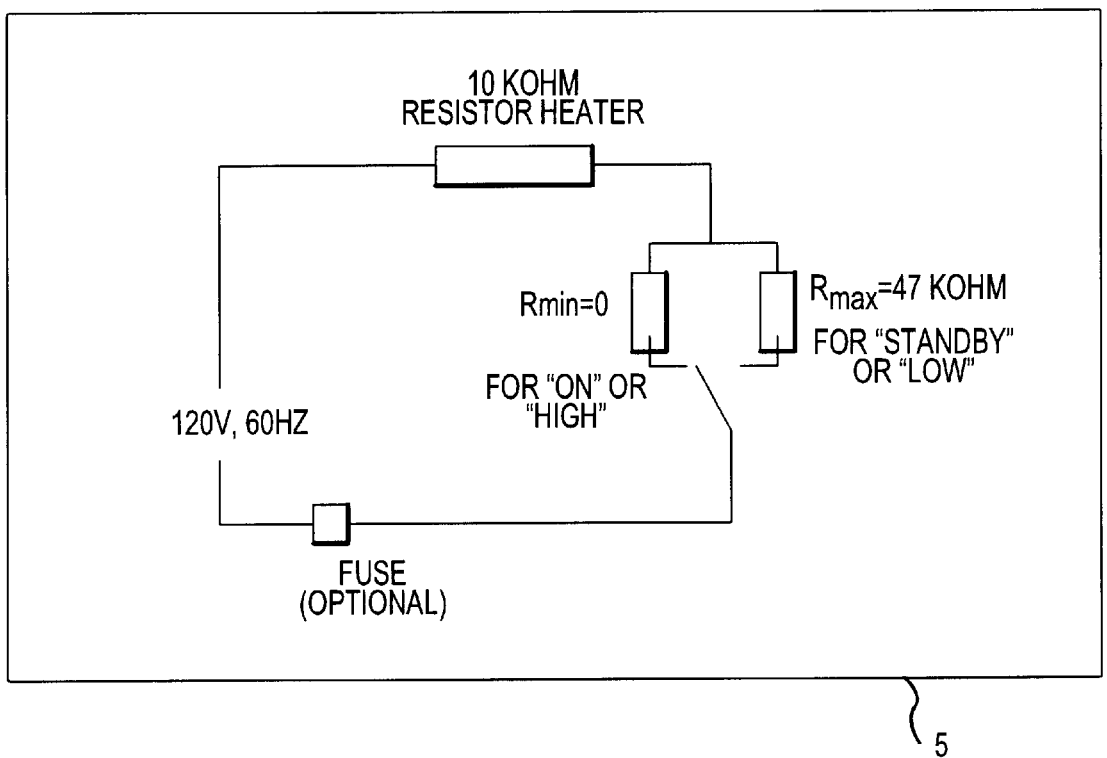
FIG. 11 is a schematic of a resistor-type heating element in accordance with one exemplary embodiment of the present invention.

Housing unit 12 suitably includes a vent system 16 and an electrical plug unit 18. Bottle unit 14 is configured for receipt of a vaporizable liquid material. In accordance with various aspects of the present invention, the vaporizable material can be any number of conventional materials dispensed from vapor vaporizers including fragrances, disinfectants, sanitizing agents, insect repellants, insecticides and the like. Preferably, and in accordance with one aspect of the present invention, the material to be volatilized comprises a fragrance material and system 10 is used as an air freshening device. In this manner, refill bottle unit 14 is suitably filled with a fragrance containing material and is inserted into housing unit 12 such that the fragrance material can be vaporized through operation of a heater unit which promotes or encourages vaporization from the wick. For example, FIG. 8 illustrates an exemplary embodiment of the positioning and placement of wick, and FIG. 10 illustrates a general region 17 to be heated on wherein the wick is to be heated. The vaporized fragrance passes through vent system 16 to the environment.

In accordance with various aspects of one embodiment of the present invention, electrical plug unit 18 is plugged into a conventional electrical outlet thereby causing a heater unit to heat the liquid and vaporize the liquid that has been drawn up into the wick and allow the same to escape through the openings in vent system 16. The term "vaporized" as used herein is used in a conventional sense and is intended to include not only the formation of vapors but also the formation of small aerosol sized particles which, as is known in the art, may be generated by actuation of such device.

Actuation of the heater, in one exemplary embodiment, may be accomplished by operation of, for example, a three-position rocker switch 5 as depicted in FIG. 7. A first setting of rocker switch 5 may correspond to a high-delivery fragrance setting, a second setting of rocker switch 5 to a stand-by fragrance delivery setting, and a third setting of switch 5 corresponding to the liquid vaporizer 10 being turned off. It will be appreciated by those skilled in the art, however, that actuation of the heating element may alternatively be readily accomplished by other means, such as for example, a dial, a slide, a lever, digital control circuitry or any of various other means capable of allowing selectable functionality, now known or hereafter devised by those skilled in the art.

While any heater unit may be used, preferably the heating unit comprises a heating element that can be readily and reliably charged through use in a conventional outlet. In such a manner, heating element (not shown) is electrically connected to plug unit 18. Any conventional heating units may be utilized, as will be readily recognized by those skilled in the art. Similarly, and as is generally shown in the various figures, plug unit 18 may be any conventional plug unit and may be oriented in any particular direction, or even configured for rotation within housing unit 12.

Figure 6:
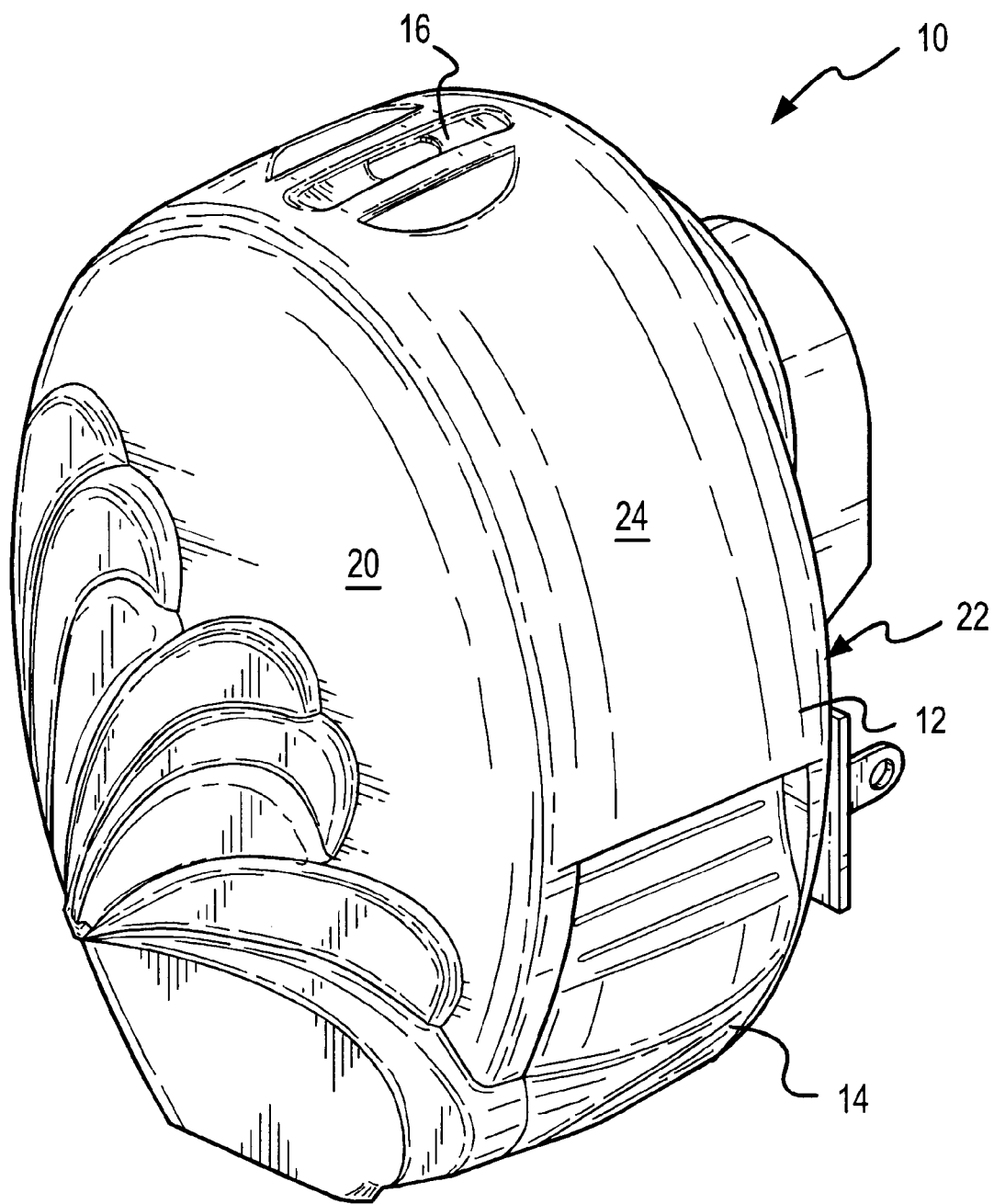
FIG. 6 is a perspective view of a liquid vaporizer with a resistor-type heating element in accordance with the present invention.
Figure 9:
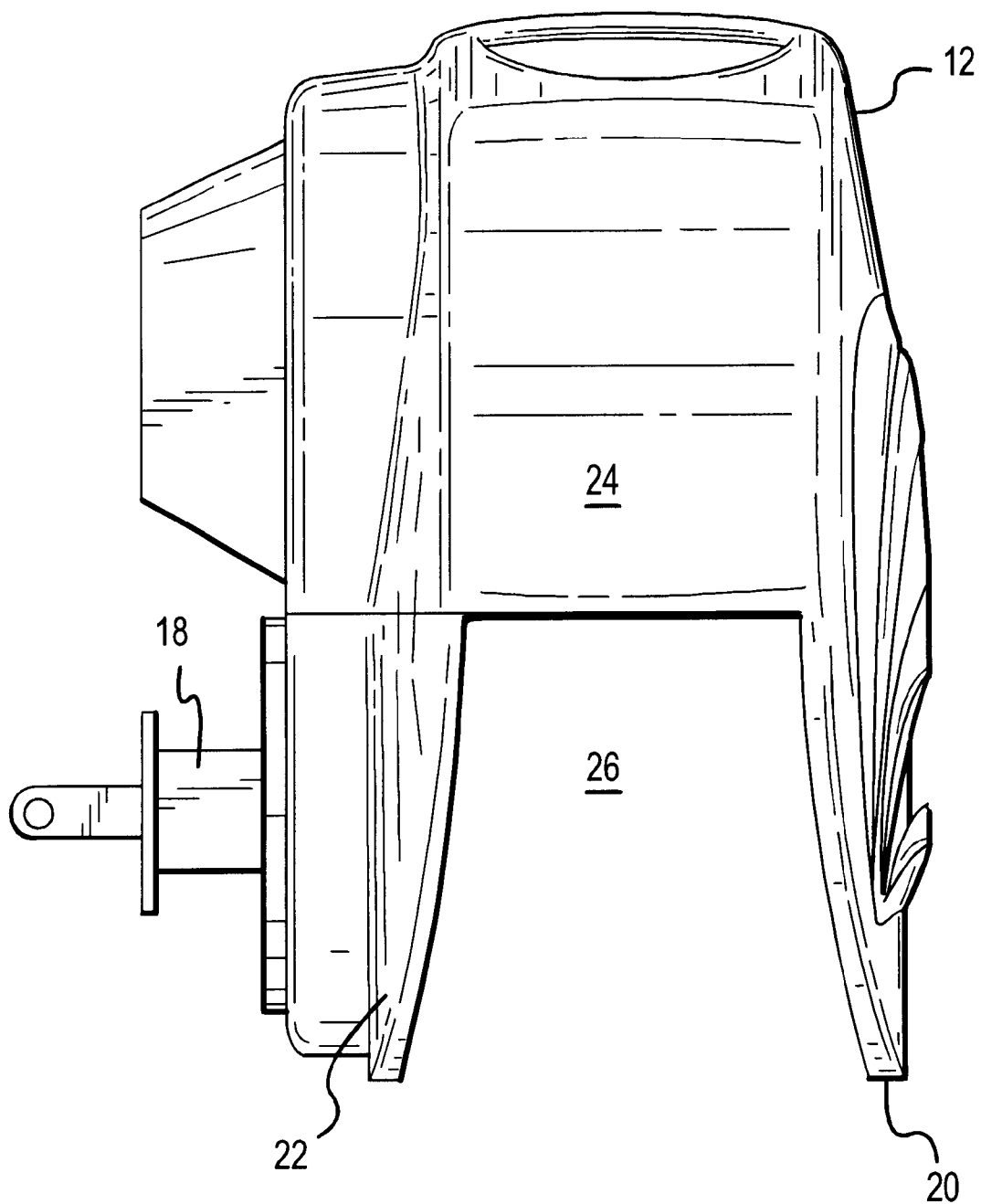
FIG. 9 is a side view of the housing unit shown in FIG. 8.

With continued reference to FIG. 6, and with further reference to FIGS. 7 and 10, an exemplary housing unit 12 is configured to include a housing front surface 20, a housing back surface 22 and an interconnecting top surface 24. Preferably, as shown best in FIGS. 7, 9 and 10, housing unit 12 is configured with a partially open bottom 26, which is configured for receipt of refill bottle unit 14.

Front surface 20 of housing unit 12 suitably is provided with a decorative element. Preferably, refill bottle unit 14 and housing unit 12 are interconnected in a "snap-and-fit" manner and preferably the design element contained on front housing 20 is suitably configured for such purposes. That is, preferably an element on bottle unit 14 is suitably configured to cooperate with a portion of housing front wall 20 to provide the "snap-and-fit" configuration and thus, interconnect bottle unit 14 and housing unit 12. It will be appreciated by those skilled in the art that various projection configurations may be utilized to enable bottle unit 14 to be interconnected with housing unit 12 and the configuration set forth in the drawing figures is for illustrative purposes only. Other configurations now known or hereafter devised by those skilled in the art may also be used.

As shown, for example, in FIGS. 6 and 7, preferably, housing unit 12 and refill bottle unit 14 fit together to provide a uniform profile system 10. However, it should be appreciated in accordance with various embodiments of the present invention, refill bottle 14 may be suitably configured to be larger than housing unit 12 or alternatively smaller than housing unit 12. Additionally, refill bottle 14 may be configured to extend beyond housing 12 or in any other shape as is now known or hereafter devised by those skilled in the art.

Preferably, bottle 14 is suitably sized for use in connection with household use. In accordance with various aspects of the present invention, bottle 14 preferably is configured for receipt of between about 25 to about 75 milliliters of liquid material, more preferably from about 35 to about 50 milliliters of liquid. In the presently described, non-limiting embodiment, the weight and moment of the device/system, inclusive of the refill bottle, is such that the center of gravity is appropriately positioned and the weight is less than that which would otherwise cause the device/system to be unstable within the outlet.

Preferably, refill bottle 14 is a conventional bottle or similar device configured to receive a volatilizable material and hold a wick 40 firmly in place. Generally, wick 40 will be secured to refill bottle 14 by a wick securement system 42. Wick securement system 42 preferably includes a wick retaining element and an attachment ring. Preferably, wick 40 is secured within wick retainer, which in turn is attached to attachment ring which is crimped or otherwise attached to neck 58 of refill bottle 14.

Neck 58, as shown, for example, in FIG. 8, is preferably threaded and thus includes a plurality of threads 64. Threads 64 are suitably configured to receive, for example, a cap for securing refill bottle 14 prior to use. As shown best in FIG. 8, wick 40 extends substantially to the bottom 59 of refill bottle 14.

In the present exemplary embodiment, refill bottle 14 comprises a plastic material that is compatible with the material to be vaporized. For example, refill bottle 14 may be formed of polypropylene (which may be clarified), barex and/or PET. Similarly, housing 12 suitably comprises a plastic material, such as polypropylene or high-density polyethylene. However, in certain applications, it may be desirable for bottle 14 to be formed of other materials such as glass or the like. In accordance with various aspects of the present invention, wick securement system 42 may be suitably comprised of plastic, metal or other materials. It should be appreciated that the particular composition of refill bottle 14, securement system 42 and/or housing 12 may be modified to any material composition as is now known or hereafter devised by those skilled in the art.

Wick 40 may be formed from any conventional wick material. Suitable wick materials include porous/sintered plastics such as high density polyethylene and polypropylene, bonded fibers, glass sintered fibers, ceramic materials, carbon fibers, sintered carbon, wood, compressed wood composites bundled or woven material fibers, bundled or manmade fibers. In general, wick 40 can be formed of any suitable material now known or hereafter devised by those skilled in the art.

As briefly mentioned above, in accordance with one aspect of the present invention, electrical switch 5 changes the amount of heat generated by suitably providing varying resistance in the electric circuitry of the vaporizer 10. By changing the switch position 5, the resistance value varies within a specified range ($R_{min}$ to $R_{max}$). $R_{min}$ controls the maximum operating temperature of the wick and thus maximum level of fragrance released from the vaporizer. For example, $R_{min}$ is suitably set at such a value that at an ambient temperature of 25° C., the maximum wick temperature is between about 49° C. and 88° C., and preferably between 54° C. and 82° C. It should be appreciated that other temperature ranges that may be below, above and/or partially inclusive of the foregoing ranges, fall within the scope of the present invention.

Generally, the value of $R_{min}$ may be determined by the technical parameters of the heating element used. For example, in accordance with one exemplary embodiment of the present invention and as shown in FIG. 7, an electric vaporizing vaporizer 10 containing a resistor-type heating element comprises a "High/Standby/Off" or "High/Low/Off" type fragrance switch 5. In another exemplary embodiment, the unit also may include a non-polarized plug capable of 90-degree rotation. When turned to the "High" position, the unit suitably maintains a steady wick temperature of about 51° C. (measured at the top tip of the wick). When turned to the "Standby" position, the wick temperature is decreased to about 24° C., or otherwise slightly higher than the ambient room temperature of about 23° C. The vaporizer may be readily redesigned to adjust the fragrance output at the "High" position by varying the resistance of the heating element or the $R_{min}$. The fragrance output at the "Standby" or "Low" position can also be readily adjusted by altering the $R_{max}$.

In accordance with one aspect of the present invention, $R_{max}$ suitably controls the minimum wick temperature and minimum level of fragrance release from the vaporizer. $R_{max}$ is set at a value such that the minimum wick temperature is greater than the ambient temperature but less than the maximum wick temperature. Thus, by selecting different values of $R_{max}$, the minimum wick temperature can be set to substantially deliver a continuous weaker but significantly fragranced environment. In such cases, the fragrance switch can be typified as "High/Low" for fragrance control. Alternatively, the $R_{max}$ can be adapted such that fragrance delivery is slow enough that consumers will hardly notice it. In this case, the fragrance switch 5 can be typified as "On/Standby."

In accordance with various aspects of the present invention, the effective resistance of an exemplary fragrance switch 5 may include a single resistor, a variable resistor, sets of multiple resistors in parallel or series arrangements as well as other resistive means well known in the art. For example, as depicted in FIGS. 12A, 12B and 12C, the resistor $R_{max}$ and/or $R_{min}$ connected to the fragrance switch 5 can be a single resistor (as depicted in FIG. 12A), a variable resistor (as depicted in FIG. 12B), or a set of multiple resistors in parallel or series arrangement (as depicted in FIG. 12C). The effective resistance values are suitably selected to meet the criteria described for $R_{max}$ and $R_{min}$ to deliver satisfactory product performance and fragrance delivery control.

In contrast to a typical ON/OFF type electrical switch that cuts-off the current at the "OFF" position, it is possible for a fragrance switch 5, in accordance with an exemplary embodiment of the present invention, to continuously permit an electrical current passing through the heating element of the fragrance vaporizer, regardless of where the switch 5 is placed. Thus, the assembly process is simplified as well as making the device suitably adaptable to most outlets.

In accordance with various alternative aspects of the present invention, the heating element may be suitably configured to prevent overheating caused by electrical surges. For example a positive temperature coefficient (PTC) thermistor has such properties. That is, a PTC suitably adapted to adjust its resistance to compensate for variations of electrical voltage or current in a specified range. Within this range, the energy output of the vaporizer and the wick temperature can generally be maintained with respect to the corresponding voltage/current flux.

Figure 13:
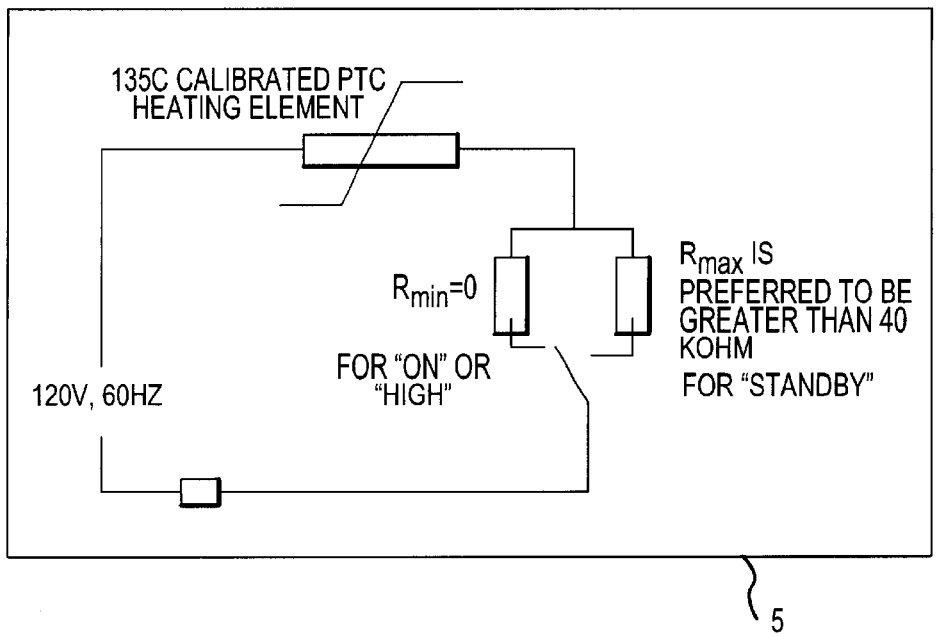
FIG. 13 is a schematic of a PTC-type heating element in accordance with another exemplary embodiment of the present invention.

For example, FIG. 13 depicts a plug-in liquid electric air freshener with the housing configuration shown in FIG. 7 further including a PTC-type heating element. Exemplary technical parameters of the PTC are shown in Table 1 below. After the unit is activated, the input voltage is varied from 110V to 140V. As shown in Table 2, in response to the voltage increase, the resistance of the PTC increases to maintain the wattage at substantially the same level. As a result, the wick temperature and the fragrance evaporation remain approximately the same although the voltage is increased.

TABLE 1

Technical parameters of the PTC

| Technical Parameters | |
|---|---|
| Heater lid (top) | Nylon 66 + Glass Fiber, wt = 4 g |
| Heater enclosure (bottom) | Nylon 66 + Glass Fiber, wt = 4 g |
| Shape | toroidal |
| Color | Black |
| Dimensions | Outer diameter 30 mm |
| | Inner diameter: 10 mm |
| | Assembled height: 16 mm |
| PTC stone | A semiconductor on a ceramic base. |
| Material | Ceramic resistor |
| Thermal Characteristics | Reference temperature: 110° C. |
| | Surface temperature at Vmax = |
| | 135° C. ± 7° C. |
| Dimensions | Diameter: 8 mm +/− 0.5 mm |
| | Thickness: 3 mm +/− 0.1 mm |

TABLE 2

Current rating, wattage, and wick temperature with different input voltages

| Input Voltage (Vac) | Current rating (mA) | Wattage (W) | Wick Temperature (° C.) |
|---|---|---|---|
| 110 | 15.8 | 1.7 | 78 |
| 120 | 14.5 | 1.7 | 80 |
| 130 | 13.5 | 1.7 | 81 |
| 140 | 12.7 | 1.8 | 82 |

In accordance with another aspect of the previously described embodiment, resistance values are varied from 0 ($R_{min}$ always at zero) to $R_{max}$. When switch 5 is set to the position where the resistance incorporated is zero ($R_{min}$), the PTC type of heating element generally provides a maximum wick temperature for the evaporative release of fragrance. When switch 5 is set to $R_{max}$, a resistor having large resistance value is incorporated into the circuit. The resistance value typically must be large enough to reduce the electrical current and thus the PTC temperature to a low level that is beyond the range for PTC compensation.

Figure 14:
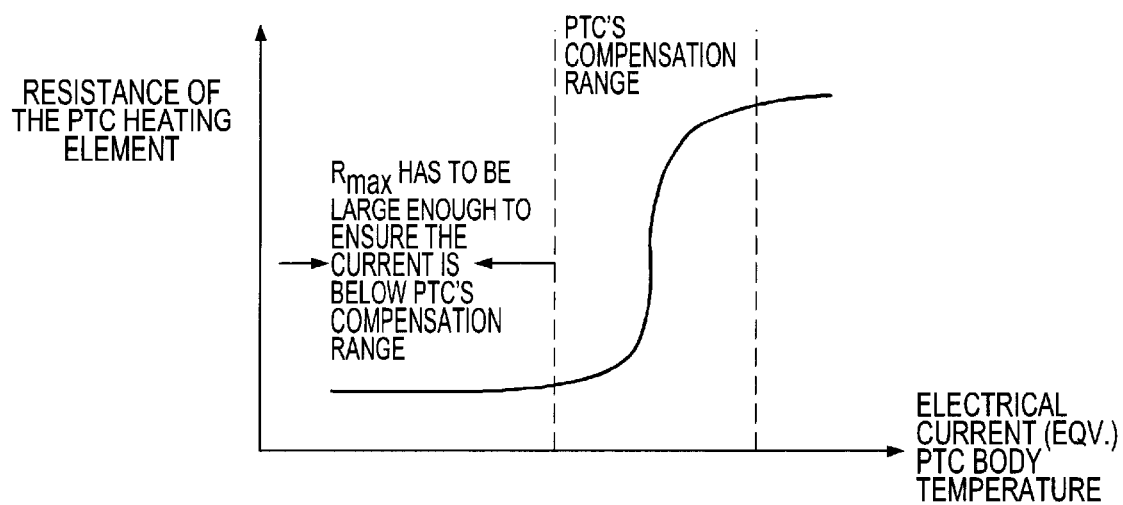
FIG. 14 is a graph showing resistance versus current for PTC-type heating elements in accordance with one exemplary embodiment of the present invention.

For the electric liquid vaporizer with the PTC type heating element, a "HIGH/LOW" or "HIGH/STANDBY" type switch for fragrance control may be incorporated as shown in FIG. 13. As switch 5 is set to a position where the effective resistance is zero, the vaporizer heats the wick to the maximum operating temperature between 60°–66° C., and significant fragrance delivery may be observed. Alternatively, as shown in FIG. 14, as switch 5 is set to $R_{max}$, a large resistor is incorporated such that the current rating is significantly reduced to a level beyond the PTC's capability for compensation.

As shown in Table 3 below, the correlation among the $R_{max}$, body temperature of $R_{min}$, current rating, and wick temperature is shown. The results show that when the $R_{max}$ is generally small (e.g., <1 Kohms), the tendency of current reduction is compensated by the PTC. In one exemplary embodiment, the $R_{max}$ in Table 3 is preferred to be greater than 31.7 Kohm so that the actual energy consumption is within the limit of the energy rating of $R_{max}$.

In contrast, when a large $R_{max}$ is selected (e.g., 47 or 93.6 Kohms), the current draw is significantly dropped indicating that the PTC becomes incapable of compensating the effect. As a result, the wick temperature is significantly reduced to about 25°–28° C.; only slightly higher than the ambient room temperature of about 21° C. Therefore when switch 5 is pointed to the $R_{max}$ position, the vaporizer unit only allows very slow fragrance evaporation and provides consumers the option to have the unit in a "STANDBY" status.

Thus, the present invention provides means for controlling the temperature of the heating element of a vaporizer device. Additionally, though the present invention has been described with reference to various preferred embodiments, various principles and applications of the present invention have been described by way of the preceding exemplary embodiments; other combinations and/or modifications of the above-described structures, arrangements, applications, proportions, elements, materials or components used in the practice of the present invention, in addition to those not specifically recited, may be varied or otherwise particularly adapted by those skilled in the art to specific environments, manufacturing or design parameters or other operating requirements without departing from the general principles of the same. For example, various changes in the configuration of the housing unit, plug unit and/or heating unit may be made without departing from the scope of the present invention. Moreover, wick temperature control mechanisms may be augmented or modified in accordance with the various teachings herein as well as other configurations known in the art and not described herein. Accordingly, these and other changes or modifications are intended to be included within the scope of the present invention as set forth in the appended claims.

TABLE 3

Influence of different resistor ($R_{max}$) values on alternating current, body temperature of the $R_{max}$, energy consumption by $R_{max}$, and wick temperature

| Resistor value (Kohms) | $R_{max}$ energy rating (W) | Actual energy consumption by $R_{max}$ (W) | Actual body temperature of $R_{max}$ (° C.) | Equilibrium Alternating Current Draw (mA) | Wick Temperature (° C.) |
|---|---|---|---|---|---|
| 0 (at the "High" position) | N/A | N/A | N/A | 16.6 | 77 |
| 9.9 | 0.5 W | 1.4 W | 93 | 11.8 | 36 |
| 21.8 | 0.5 W | 0.6 W | 65 | 5.3 | 28 |
| 31.7 (two resistors (10K + 22K) in series | 0.5 W | 0.4 W | 10K-33 22K-39 | 3.7 | |
| 47.0 | 0.5 W | 0.3 W | 44 | 2.5 | 26 |
| 93.6 | 0.5 W | 0.1 W | 38 | 1.2 | 25 |

We claim:

1. A method of dispensing a volatile substance comprising the steps of:

providing a temperature variable heating element configured as a PTC element and a resistor combination, said PTC element having a compensation range having an upper limit and said resistor having a maximum resistance;

providing a reservoir and volatile substance to be dispensed therefrom; and varying the temperature of said variable heating element by selecting said maximum resistance to be greater than about 11000 KOhms such that electrical current through said resistor is reduced to below said upper limit of said compensation range of said PTC element, thereby maintaining the temperature of said heating element at about 25° C.

2. A vapor dispensing apparatus comprising:

a housing for engaging a reservoir and positioning a wick proximate to a heating element, said reservoir comprising a bottle for containing a volatile substance and wherein said wick is in fluid communication with said volatile substance such that said volatile substance can be dispensed from said reservoir via said wick; and a temperature variable heating element configured as a PTC element and a resistor combination, said PTC element having a compensation range having an upper limit and said resistor having a maximum resistance of greater than about 11000 KOhms, said maximum resistance selected such that electrical current through said resistor is reduced to below said upper limit of said compensation range of said PTC element, thereby maintaining the temperature of said wick near an ambient temperature.

3. A vapor dispensing apparatus according to claim 2, further comprising a temperature variable heating element having minimum and maximum resistance settings in the range of about 0–95 Kohms.

4. A vapor dispensing apparatus according to claim 2, wherein said variable heating element has a minimum resistance setting corresponding to a wick temperature of about 49°–88° C.

5. A vapor dispensing apparatus according to claim 2, wherein said variable heating element has a maximum resistance setting corresponding to a wick temperature of about 25° C.

6. A vapor dispensing apparatus according to claim 2, wherein said variable heating element comprises a maximum resistance setting corresponding to said heating element being turned off.

* * * * *